(12) United States Patent
Lehmann et al.

(10) Patent No.: US 6,804,873 B2
(45) Date of Patent: Oct. 19, 2004

(54) METHOD FOR MANUFACTURING CONTAINERS AND APPARATUS

(75) Inventors: Martin Lehmann, Obere Fahrnbühlstrasse 1, CH-5610 Wohlen (CH); Jürgen Steck, Bexbach (DE); Karsten Riemer, Homburg (DE)

(73) Assignee: Martin Lehmann, Wohlen (CH)

( * ) Notice: Subject to any disclaimer, the term of this patent is extended or adjusted under 35 U.S.C. 154(b) by 0 days.

(21) Appl. No.: 10/284,196

(22) Filed: Oct. 31, 2002

(65) Prior Publication Data

US 2004/0083814 A1 May 6, 2004

(51) Int. Cl.$^7$ .................................. G01R 4/00
(52) U.S. Cl. ........................... 29/593; 73/588
(58) Field of Search ............ 73/588, 582, 584, 73/589, 592, 590, 405; 29/592.1, 593

(56) References Cited

U.S. PATENT DOCUMENTS

| | | | |
|---|---|---|---|
| 4,320,659 A | * 3/1982 | Lynnworth et al. | 73/589 |
| 5,029,464 A | 7/1991 | Lehmann | 73/49.3 |
| 5,170,660 A | 12/1992 | Lehmann | 73/49.3 |
| 5,239,859 A | 8/1993 | Lehmann | 73/49.2 |
| 5,317,801 A | * 6/1994 | Tanaka et al. | 29/830 |
| 5,372,042 A | 12/1994 | Jarman et al. | 73/588 |
| 5,907,093 A | 5/1999 | Lehmann | 73/49.2 |
| 5,915,270 A | 6/1999 | Lehmann | 73/49.2 |
| 6,047,602 A | * 4/2000 | Lynnworth | 73/632 |
| 6,082,184 A | 7/2000 | Lehmann | 73/49.3 |
| 6,202,477 B1 | 3/2001 | Lehmann | 73/49.3 |
| 6,251,203 B1 | * 6/2001 | Vala et al. | 156/73.1 |

FOREIGN PATENT DOCUMENTS

JP    2000/221173    8/2000

OTHER PUBLICATIONS

"High contrast ultrasound images of defects in food package seals", Catherine H. Frazier et al., IEEE Transactions of ultrasonics, ferroelectrics, and frequency control, vol. 47, No. 3, May 2000.
J. Krautkramer, H. Rautkramer: "Werkstoffprufung mit Ultraschall" 1980, Springer–Verlag, Berline Heidelberg New York XP002248630 p. 512, paragraph 2—p. 513, last paragraph,; figures 27.4, 27.5.

* cited by examiner

Primary Examiner—Hezron Williams
Assistant Examiner—Jacques M. Saint-Surin
(74) Attorney, Agent, or Firm—Antonelli, Terry, Stout & Kraus, LLP

(57) ABSTRACT

A method of manufacturing filled containers includes providing at least a first and a second part of the container, providing a product within at least one of the first and second parts, and assembling the first and second parts by bonding a portion of the first part to a portion of the second part, thereby generating a bond area. Scanning along the bond area is performed with a transmitted beam of a pulse train of ultrasonic energy. A reflected pulse train of ultrasonic energy from the bond area is sensed and a time derivative of at least one of time lag and of amplitude of the sensed pulse train is determined. A signal indicative of the quality of the bond along the bond area is generated by comparing at least one of the time derivatives with a predetermined threshold valve. If the indicative signal indicates a bond along the bond area is inaccurate, the container is separated. An apparatus for testing filled containers is also disclosed.

68 Claims, 10 Drawing Sheets

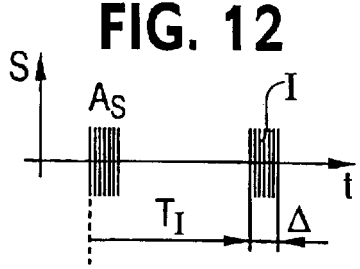
FIG. 12
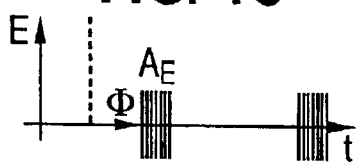
FIG. 13
FIG. 14
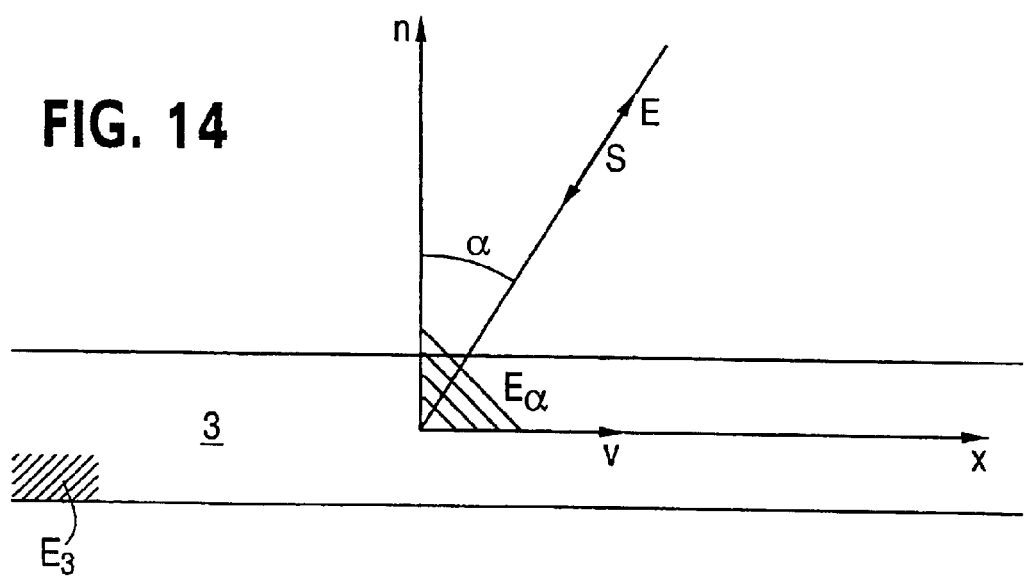
FIG. 15
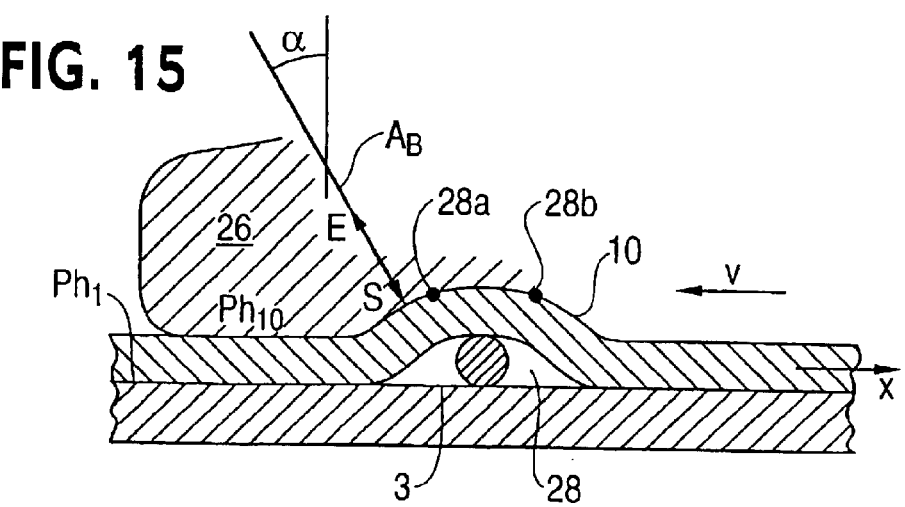

FIG. 16
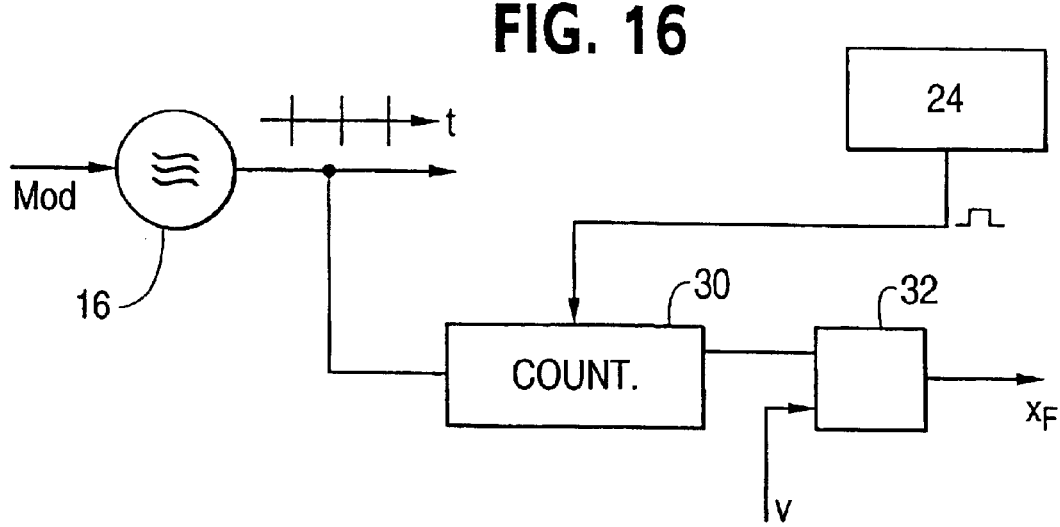
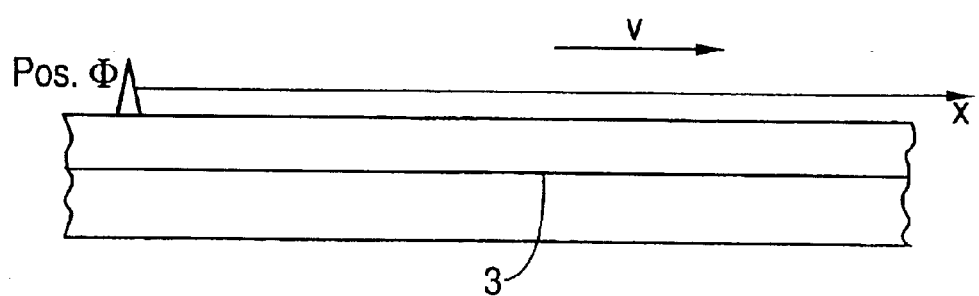
FIG. 17
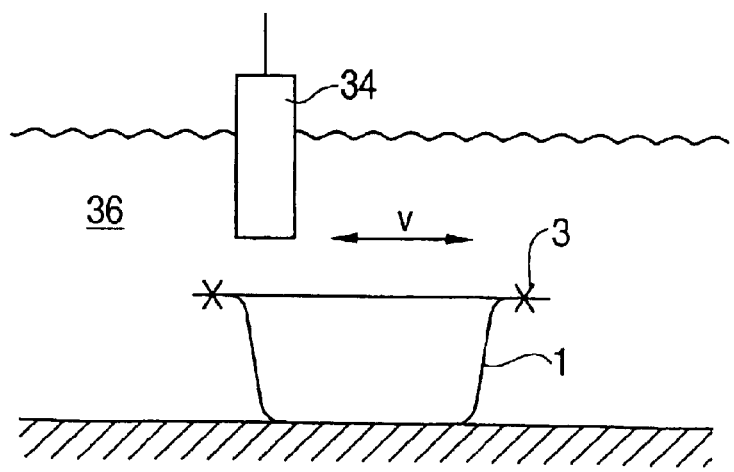

METHOD FOR MANUFACTURING CONTAINERS AND APPARATUS

The present invention departs from problems which are encountered in manufacturing filled containers and as will be exemplified referring to FIGS. 1 to 10.

Figure 1:
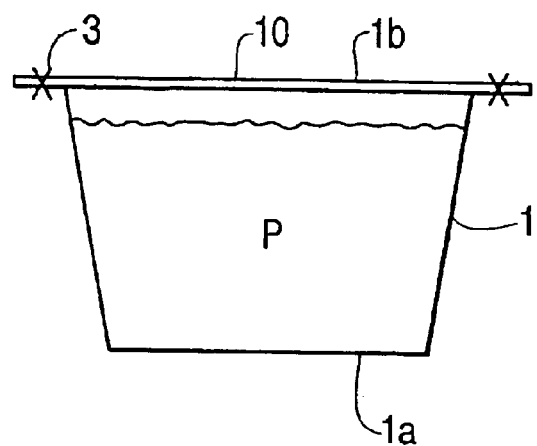

In FIG. 1 there is shown a container 1 which comprises a first part 1a and a second part 1b. The first part 1a is conceived as a receptacle and is filled with a product P as e.g. with a foodstuff, e.g. yoghurt. The second part 1b is conceived as a covering foil or lid, which is sealingly bonded to the part 1a along a bond area 3.

Figure 2:
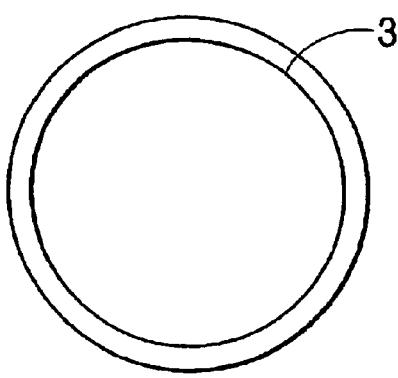
Figure 3:
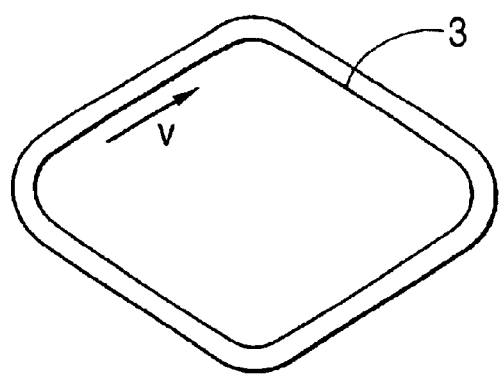
Figure 4:
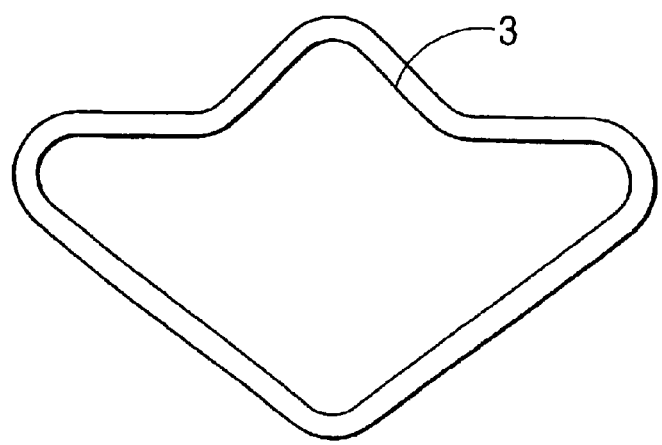

In top view the container 1 may have a great variety of shapes, some examples being shown in FIGS. 2 to 4. According to FIG. 2 the container 1 as of FIG. 1 is cylindrical or cone shaped and the bond area 3 is circular.

According to FIGS. 3 and 4 the container 1 has a shape departing from circular, conceived with a shape resulting from fantasy of the container manufacturer. There the shape of the bond area 3 largely departs from circular and may in fact have practically any looped shape.

Figure 5:
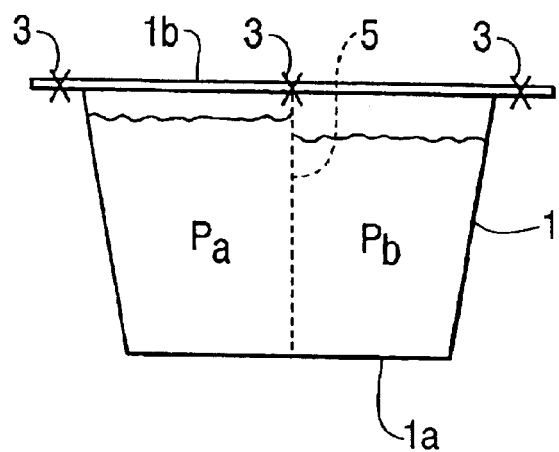

According to FIG. 5 the container 1 with an outer shape e.g. as shown in FIG. 1 has a part 1a which is filled e.g. with two filling products $P_a$ and $P_b$ in two respective compartments which are separated by a separating wall 5, e.g. being an integral part of the container part 1a. Accordingly the bonding area 3 by which the second part 1b is sealingly bonded to the part 1a of the container 1 has, as shown in top view in FIG. 6, not only a looping area but additionally an area which crosses that loop. FIGS. 7 and 8 show, departing from the container shapes as exemplified in the FIGS. 3 and 4, such containers and the resulting bonding area 3 when e.g. their part 1a according to FIG. 1 is subdivided by additional walls into two or more than two distinct compartments. From FIGS. 1 to 8 it results that the bonding area 3 may have practically any shape.

Figure 8:
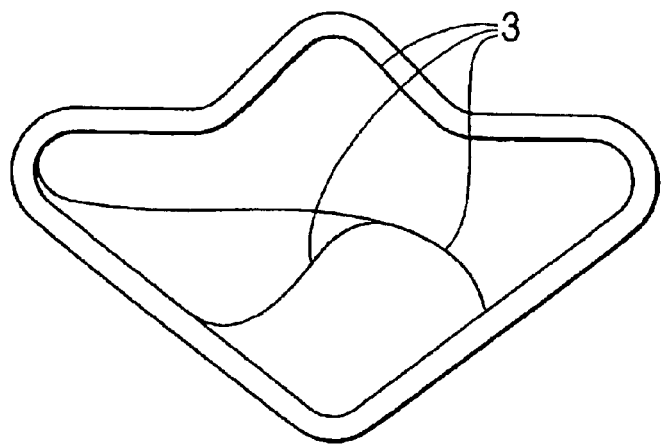
Figure 9:
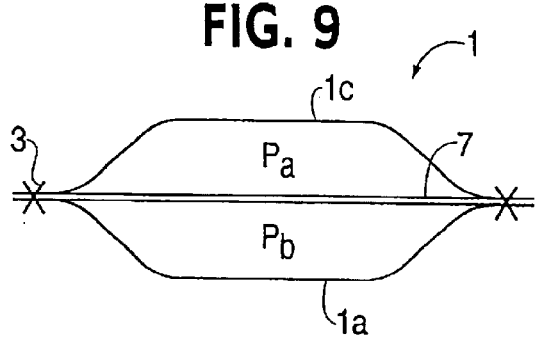

Further, and as shown in FIG. 9, the second part of a container 1 needs not be a foil or lid part, but may be a second receptacle part. According to FIG. 9 the container 1 comprises part 1a formed as a receptacle and part 1c formed as a receptacle too. These two parts are bonded along bond area 3. Thereby, the container 1 may contain one single product, so that no separation is provided within container 1. If the container 1 contains e.g. two products $P_a$ and $P_b$, which shall not be mixed within the container 1, one or even two separating foils 7 are provided and the bond area 3 preferably links the parts 1a, 1c as well as the foils 7. Additionally, the technique as shown in FIG. 9 may be combined with subdivision of the parts 1a and/or 1c by walls as shown in FIGS. 5 to 8.

Figure 6:
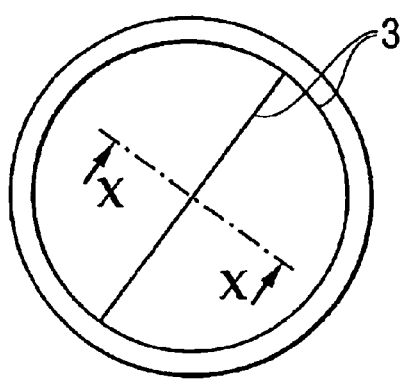
Figure 7:
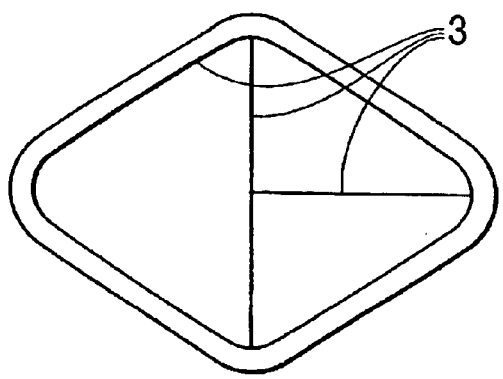
Figure 10:
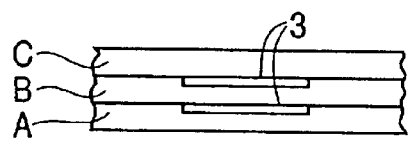

All the bond areas 3 as exemplified in the FIGS. 1 to 9 have in cross-section as shown in FIG. 6 at X—X the structure as shown in FIG. 10. Two or more than two, according to FIG. 10 e.g. three, materials A, B, possibly C . . . are as schematically shown bonded together at the bond area 3, which is in said cross-sectional view substantially flat. Thus, the bonding area 3 is in fact band-shaped. Bonding may be done by any known technique for the addressed purpose, as by gluing, welding etc. More specifically bonding may be performed in a preferred form by ultrasonic sealing, high frequency sealing or heat contact sealing. In this context the addressed "bonding" is often referred to e.g. in literature as "sealing". Further, the material as of A, B, C . . . of FIG. 10 may be, considered in subsequent pairs, equal or different, thereby being e.g. plastic material, metal material as of aluminum for foils, coated metal material etc.

We define generically surfaces along which two material phases contact each others, even if the contacting materials are equal and just lay one upon the other, as material interfaces. Thus, according to FIG. 10 a first material interface is formed between material C and ambient air, a second between material B and material C and a third between material A and B, a fourth again between ambient air and material A.

By the addressed bond areas 3 one or more than one filling product of the container 1 are encapsulated. If the bond area 3 does not provide for a high quality joint and according to the degree of bonding failure, air may be entrapped or filling product may pour out of the container 1 more or less rapidly or become entrapped too within the bond, and may start to deteriorate over time. Also other contaminants may be entrapped in the bond area. Depending on the kind of product contained in such containers, e.g. medical products, food products, a locally inaccurate or disturbed bondage along the bond areas 3 may cause tremendous problems. Thereby, an inaccurate bond along the bond area needs not necessarily be detectable by a leak testing technique, because as addressed above e.g. a material entrapped within the bond might not deteriorate the container's unleakyness, but may on shorter or longer terms cause tremendous deterioration of the filling product, up to making such container leaky only after some time of storage.

It is therefore an object of the present invention to provide a method for manufacturing containers of the kind as described with the help of the FIGS. 1 to 10, whereat an essential step of manufacturing is testing the bond area on its quality, i.e. testing "seal integrity", so as to produce such container with high quality bond, i.e. "seal" area.

From the article "High contrast ultrasound images of defects in food package seals", Catherine H. Frazier et al., IEEE Transactions on ultrasonics, ferroelectrics, and frequency control, Vol. 47, No. 3, May 2000, investigation of bond areas by ultrasonic response evaluation is known. It is an object of the present invention to improve such testing approach with respect to accuracy and reproducibility.

This is achieved under a first aspect of the present invention by the method of manufacturing filled containers which comprises the steps of providing at least a first and a second part of the container, providing a product within at least one of the first and the second part, assembling the first and the second parts by bonding a portion of the first part to a portion of the second part, thereby generating a bond area, scanning along the bond area with a transmitted beam of a pulse train of ultrasonic energy, sensing a reflected pulse train of ultrasonic energy from the bond area, determining time derivative of at least one of time lag and of amplitude of the sensed pulse train, generating a signal indicative of the quality of the bond along the bond area by comparing at least one of the time derivatives with a predetermined threshold value and separating containers if the indicative signal indicates a bond along said bond area which is inaccurate.

Thereby, in a most preferred embodiment the beam of pulse train is led towards and onto the bond area and the reflected pulse train is led from the bond area at least to a predominant part exclusively through liquid. Thereby, it is achieved that at least a predominant part of ultrasonic energy from a respective generator to the bond area and back to an ultrasonic energy sensor is exclusively led through the liquid.

In a further most preferred embodiment the beam of pulse train is directed in a direction towards and onto the bond area, which is different from perpendicularly thereto considered in a plane which is defined by a perpendicular line on the bond area and scanning direction of the beam along the bond area.

In further preferred embodiments the bond area to be investigated forms a loop, thereby preferably an at least substantially planar loop. Thereby, further preferably, the loop is at least substantially circular.

In a further preferred embodiment the bond area defines for at least three materials stacked one upon the other, whereby respectively two of the materials concomitantly form a material interface. Then sensing comprises sensing a reflected pulse train of ultrasonic energy from at least one of the material interfaces. In a bond area where two rigid materials, as e.g. a metal foil is bonded to a plastic material, three materials appear stacked one upon the other, namely the plastic material upon which resides the foil material and finally ambient air or another ambient material as a liquid, so that three material interfaces are formed. This to clarify definition and counting of material interfaces.

In a further preferred embodiment the scanned path of the pulse train of ultrasonic energy along the bond area is monitored or measured, and the location along the bond area at which the indicative signal is generated, which indicates an inaccurate bond, is identified. This allows for information about failure at a bonding station as e.g. about failure of a bonding tool.

So as to facilitate evaluation of the sensed impulse train it is further preferred to select the duty cycle and the pulse repetition frequency of the pulse train so that the pulse train as transmitted does not overlap a reflected and sensed pulse train at the sensing location. Further, in a most preferred embodiment the beam is generated substantially coaxially to an axis of highest sensitivity of ultrasonic energy sensing. An ultrasonic energy sensor defines for a reception lobe of ultrasonic energy sensing amplification. Such reception lobe defines for the addressed axis of highest sensitivity. The transmitted beam is thereby transmitted coaxially to this axis.

In a further preferred mode of operating the inventive method the direction with which the beam is directed towards and onto the bond area defines for an angle α with a perpendicular line or normal on the bond area in a plane defined by said normal and direction of scanning which angle fulfills the following conditions:

$$0° < \alpha \leq 30°,$$

preferably $$5° \leq \alpha \leq 20°,$$

and thereby most preferred the relation $$10° \leq \alpha \leq 18°.$$

A first preferred embodiment of realizing conductance of the substantial part of ultrasonic energy through a liquid is realized in that at least the bond area of the container, an output of an electrical to mechanical converter for generating the beam as well as the input of a mechanical to electrical converter for sensing the reflected pulse train are immersed into a liquid. In another preferred embodiment of realizing this ultrasonic energy conductance in a liquid is realized by establishing locally a bridge of the liquid from the said output of the electrical to mechanical converter for generating the ultrasonic beam to the bond area and then to an input of the mechanical to electrical converter for sensing the reflected ultrasonic energy. Thereby, in a further preferred embodiment the bridge of the liquid is established by applying the liquid locally on the bond area and suctioning the liquid from the bond area just after such area having been subjected to scanning.

In a most preferred embodiment water is selected as liquid. In a further preferred embodiment and with an eye on scanning technique such scanning is realized by moving the beam along the bonding area of the container which former is kept stationary. In another preferred embodiment the beam is moved whereas the container is kept stationary for the addressed scanning. In still another preferred embodiment scanning is performed by moving the container as well as moving the beam.

Still in a further preferred embodiment the trajectory path for scanning is predetermined, so that scanning movement control may be realized on the basis of such predetermined trajectory. In another preferred embodiment, whereat accuracy and repeatability of the shape of the bond area may not be predetermined accurately enough, the course of the bond area is traced as by a picturing head and the relative movement of container and beam is controlled by the tracing result.

So as to establish stable and reproducible position of the containers to be investigated, especially if no use is made of bond area tracing techniques, in a preferred embodiment the container is positioned by suctioning action, whereby the container is suctioned-drawn into a predetermined position.

Under a second aspect of the present invention to fulfill the object as mentioned above at least a first and a second part of the container are provided, at least one of these parts is filled with a product, the two parts are assembled by bonding a portion of the first part to a portion of the second part, whereby a bond area is generated. Then the bond area is scanned with a transmitted beam of ultrasonic energy and reflected ultrasonic energy from the bond area is sensed. From the sensed ultrasonic energy there is generated a signal which is indicative of the quality of the bond along the bond area. Thereby, under this aspect the ultrasonic energy from a mechanical output of an electric to mechanical converter to generate the transmitted beam onto the bond area and said reflected ultrasonic energy from the bond area towards and onto a mechanical input of a mechanical to electrical converter for sensing the reflected ultrasonic energy is performed in a liquid. This technique under the second aspect of the present invention may preferably be combined with one or more than one of the above mentioned aspects.

Under a third aspect of the invention still to fulfill the above mentioned object again there is provided at least a first and a second part of a container to be investigated, a product is provided within at least one of these two parts, the first and second parts are assembled by bonding a portion of the first part to a portion of the second part, thereby generating a bond area. The bond area is scanned with a transmitted beam of ultrasonic energy, and reflected ultrasonic energy from the bond area is sensed. There is generated from the sensed ultrasonic energy a signal which is indicative of quality of the bond along the bond area. Thereby, further, the direction of the beam of ultrasonic energy towards and onto the bond area is selected to be different from perpendicularly on said bond area and considered in a plane defined by a perpendicular line or normal on the bond area and the scanning direction. Again and also under this third aspect of the invention the above mentioned different preferred embodiments are combined by two or more than two with the invention under this aspect.

Figure 11:
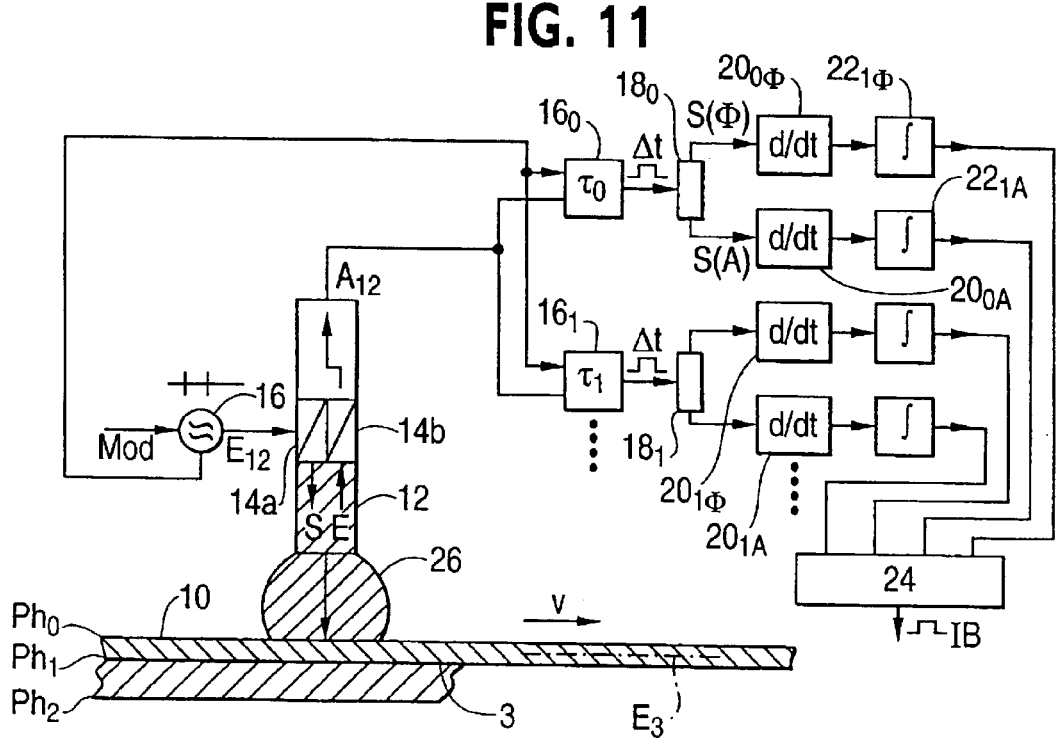
Figure 18:
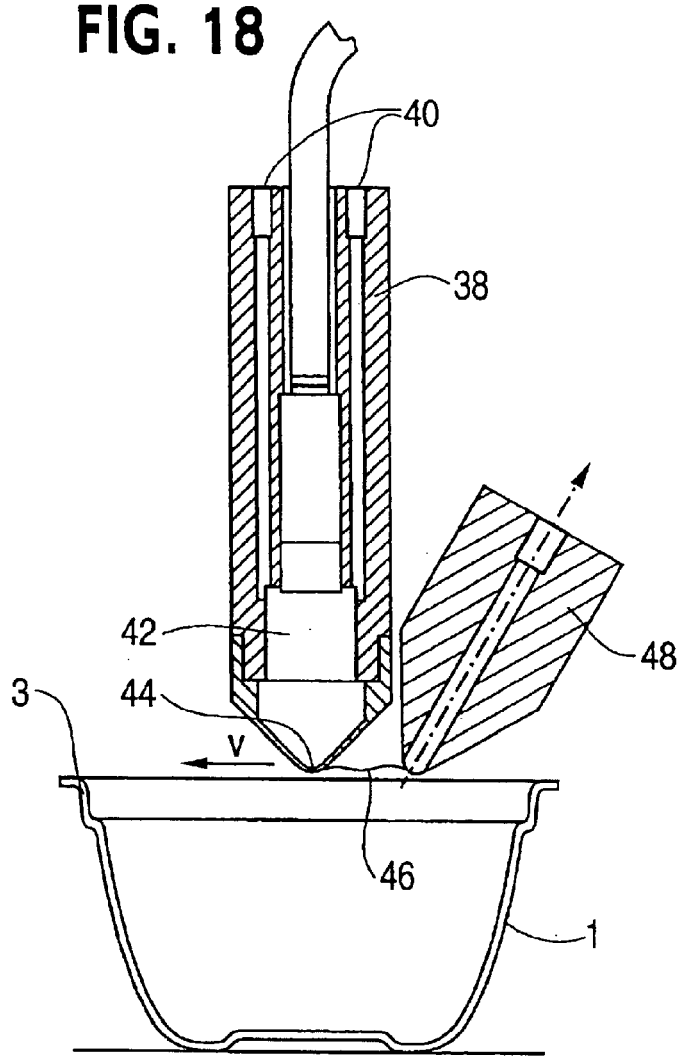
Figure 19:
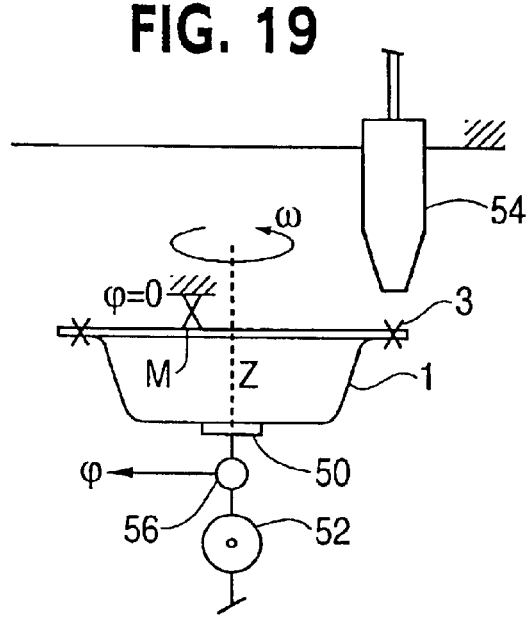
Figure 20:
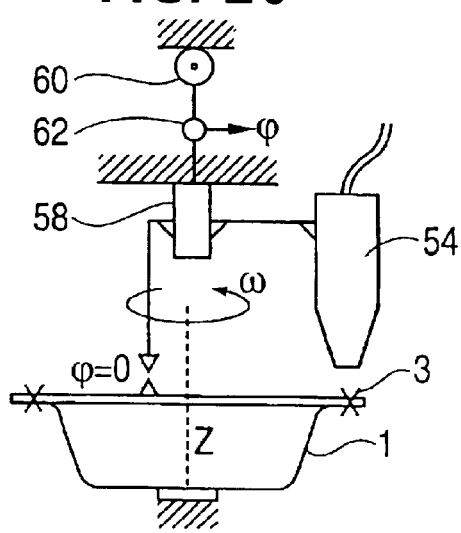
Figure 21:
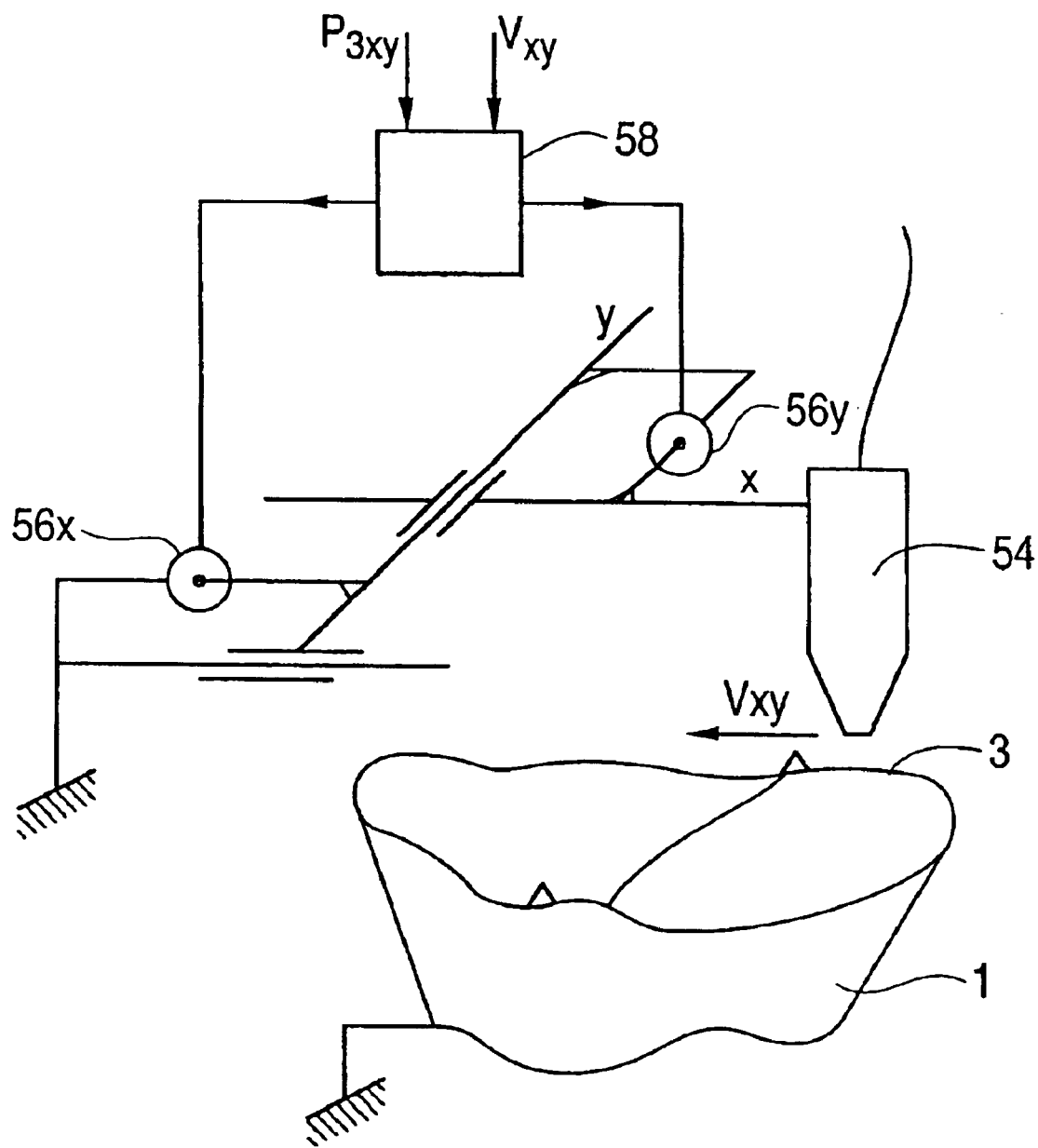
Figure 22:
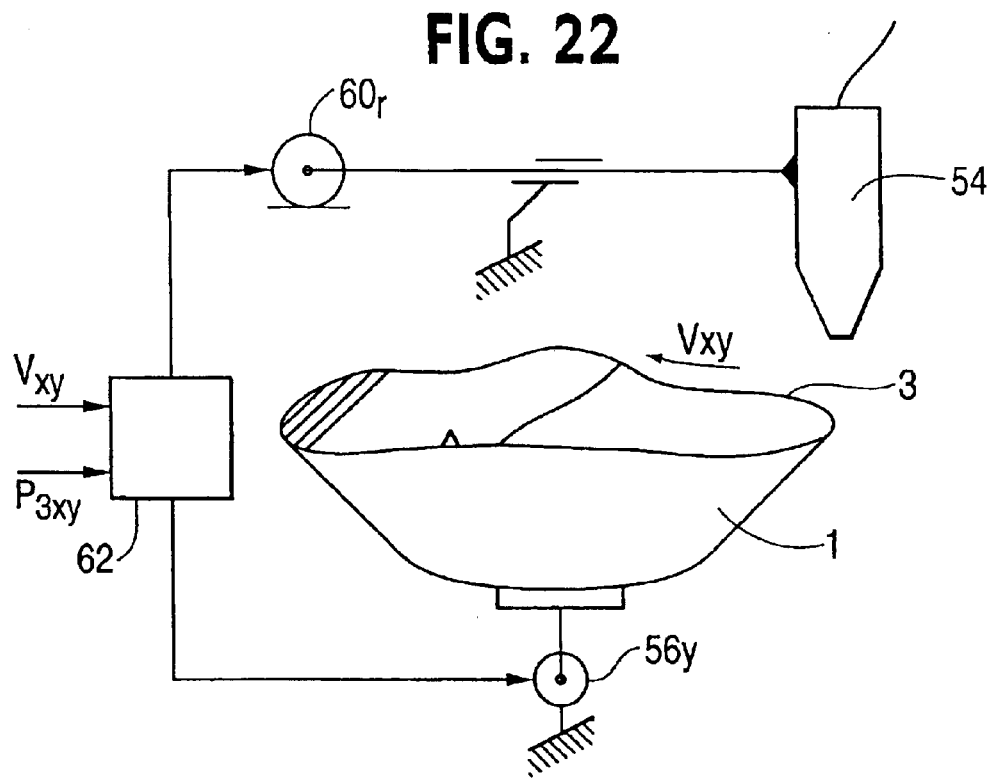
Figure 23:
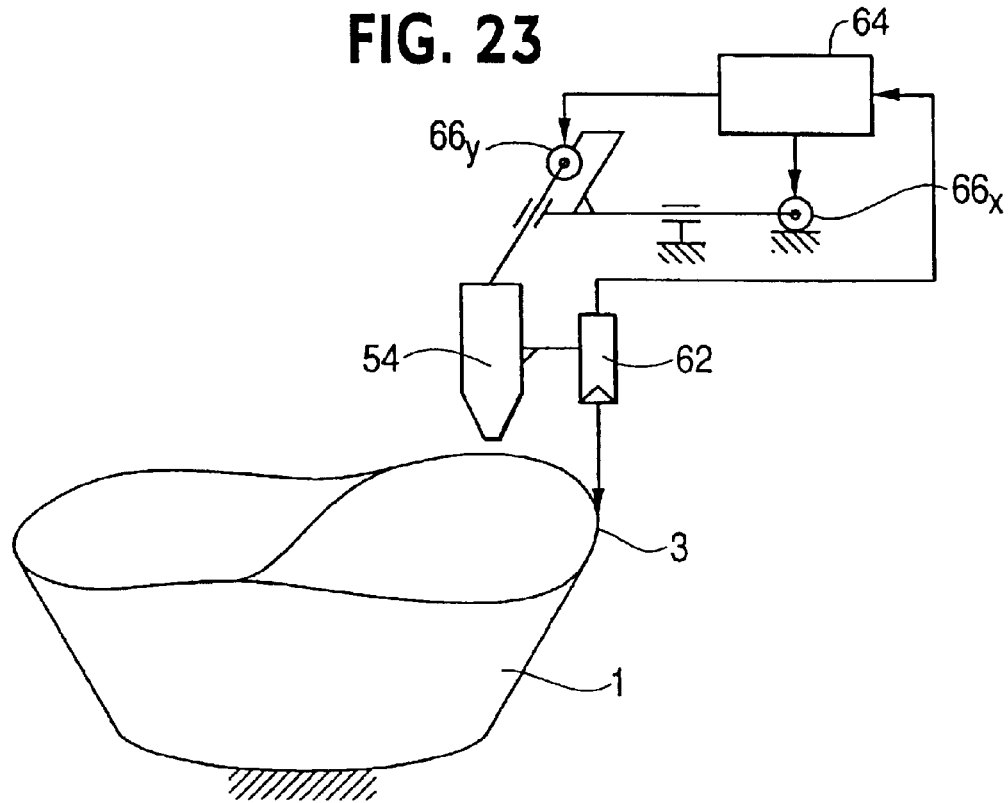
Figure 24:
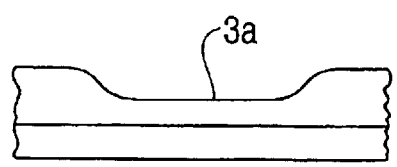
Figure 26:
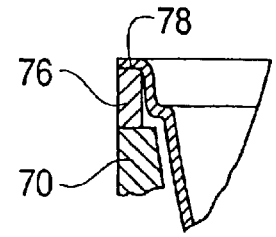
Figure 25:
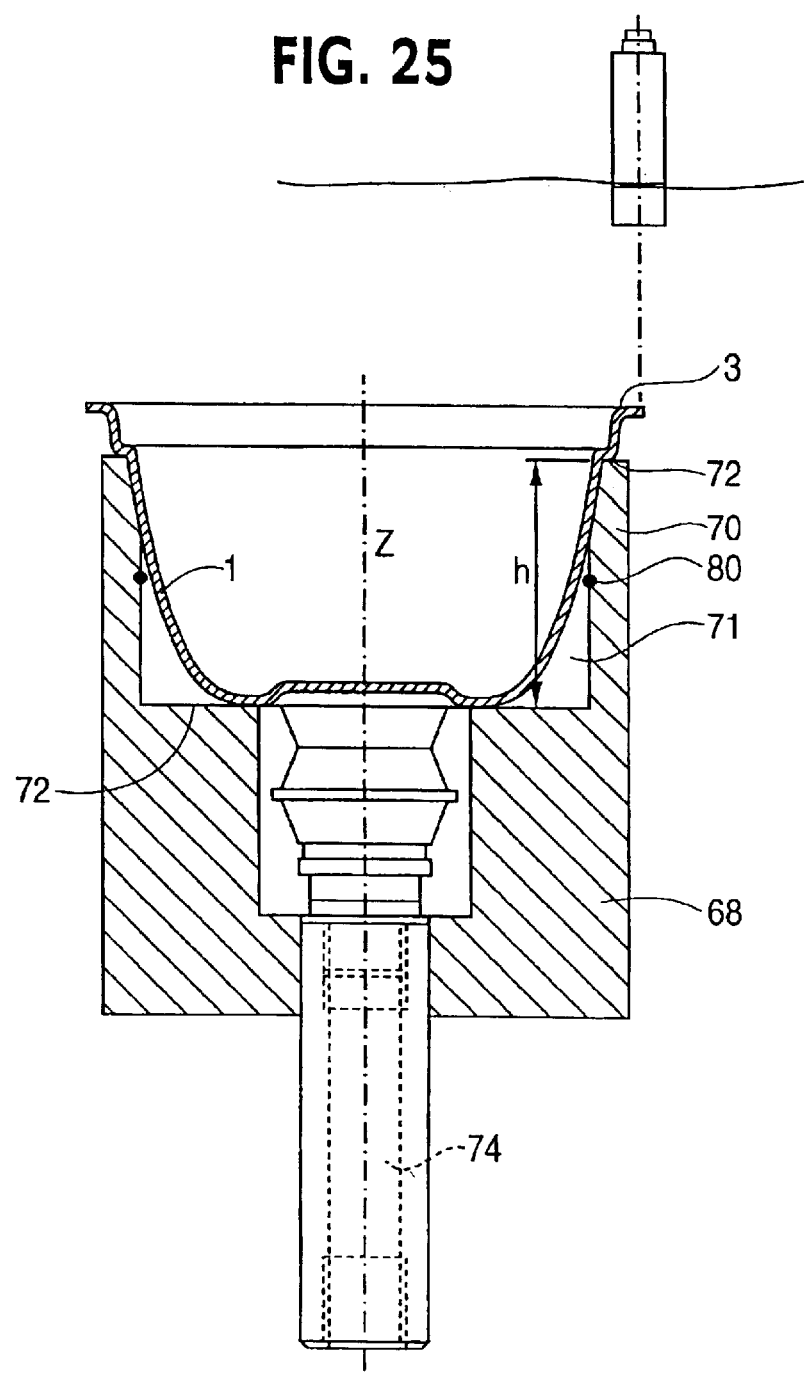
Figure 27:
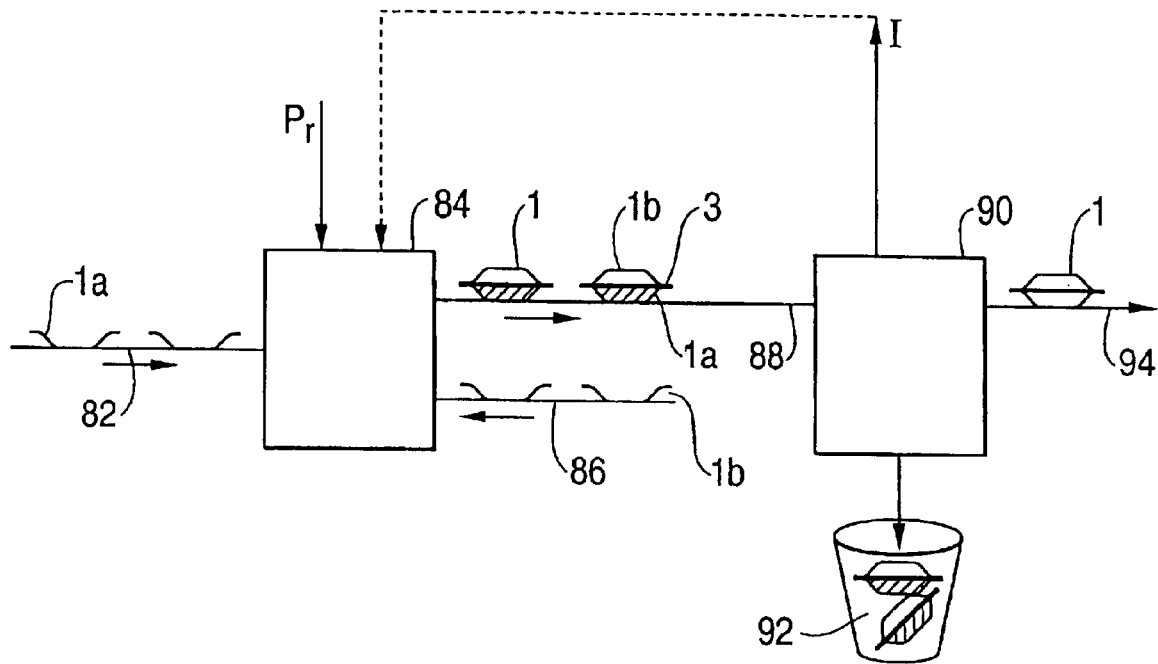
Figure 28:
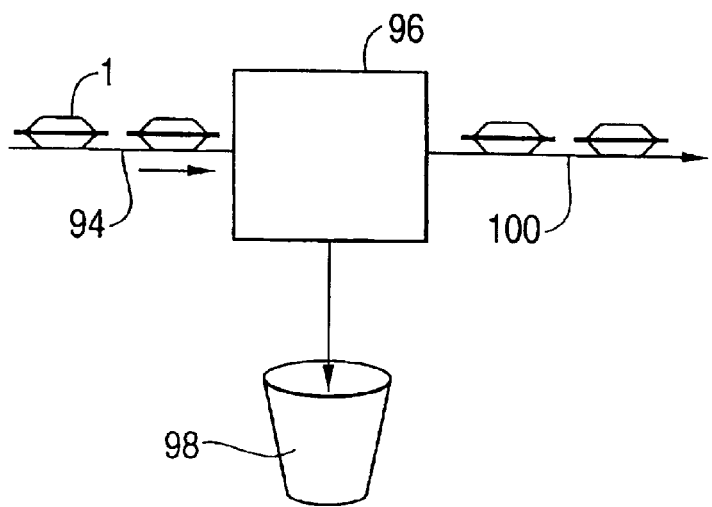

The present invention further resolves the above mentioned object by respective testing apparatus which exploit, as was addressed above under a first aspect time derivatives of ultrasonic energy, thereby especially time derivative of time lag and/or amplitude of reflected pulse train of ultrasonic energy generated by respectively transmitted pulse trains towards the bond area or by exclusively conducting,or leading ultrasonic energy from a generator output towards and upon the bond area and back to the input of an ultrasonic sensor in a liquid or by directing an ultrasonic beam as transmitted towards and onto the bond area not perpendicularly to the bond area but enclosing with a perpendicular line on the bond area an angle different from 0 and as defined in a plane comprising said perpendicular line as well as scanning direction. The present invention under all its method and apparatus aspects will now be described by examples and with the help of additional figures. These figures show:

FIG. 11 by means of a simplified functional-block/signal-flow diagram, a sensing apparatus in a preferred embodiment to perform as an essential step in the manufacturing process according to the present invention;

FIG. 12 schematically and qualitatively, an impulse train of ultrasonic energy as transmitted by the embodiment according to FIG. 11 towards and onto the bond area to be investigated;

FIG. 13 again simplified and qualitatively, a response ultrasonic impulse train as sensed by the embodiment of FIG. 11 and as reflected from one of possibly more than one material interfaces at the bond area 3;

FIG. 14 schematically, in a perspective representation, a bond area band and the angle relation of an axis of an ultrasonic beam transmitted towards and onto the bond area and preferably also of reflected ultrasonic energy with respect to a normal on the bond area band and in a plane defined by the normal and scanning direction;

FIG. 15 schematically, a spoiled or inaccurate bond area in a frequent form of appearance and a further improvement in subjecting said bond area to ultrasonic energy for inaccuracy detection;

FIG. 16 departing from the embodiment of FIG. 11 one preferred embodiment for not only detecting that the bond area is inaccurate but additionally for detecting at which location such bond area is inaccurate;

FIG. 17 schematically, one embodiment of a most preferred technique to have ultrasonic energy traveling from a transmitter to the bond area and back to a receiver exclusively in material not being ambient air, thereby being preferably a liquid;

FIG. 18 a further preferred embodiment for realization of ultrasonic energy propagation in liquid;

FIG. 19 in a schematic representation, a first embodiment for realizing scanning movement of an ultrasonic beam along a circular bond area;

FIG. 20 in a schematic representation in analogy to that of FIG. 19, a second embodiment;

FIG. 21 in a schematic perspective view, a third embodiment for realizing scanning movement of ultrasonic energy bean and bond area, making use of controlled independent, two-coordinate planar drives of the ultrasonic transmitter and receiver;

FIG. 22 in a representation in analogy to that of FIG. 20, a further embodiment whereat the transmitter/receiver is linearly moved in a controlled manner, and the container with the bond area is rotated both in a controlled dependent manner;

FIG. 23 a further embodiment for realizing the scanning movement, whereat the course of the bond area 3 is traced and the mutually relative movement of container and the bond area 3 to the ultrasonic transmitter/receiver is controlled by the traced or picked up course of the bond area 3;

FIG. 24 in a cross-sectional representation, a frequently encountered profile of bond area especially as realized by high frequency welding;

FIG. 25 in a cross-sectional representation a preferred embodiment for accurately positioning the container at least during bond area investigation;

FIG. 26 a section of FIG. 25 showing additional support of the bond area itself for some kind of containers;

FIG. 27 by means of a simplified functional block diagram, a plant for manufacturing containers according to the present invention, and FIG. 28 departing from a representation as of FIG. 27, a further improvement to integrate to bond area testing, upstream or downstream, leak testing of the closed containers.

SENSING TECHNIQUE

According to FIG. 11 there is provided, adjacent to the surface 10 of the bonding area 3, which is, under normal conditions, exposed to ambient, an arrangement of at least one ultrasonic transmitter and at least one ultrasonic receiver. Generically there may be provided more than one ultrasonic transmitter and/or more than one ultrasonic receiver, whereby the number of receivers and of transmitters do no necessarily have to be equal. Important is that the arrangement of receivers are loaded by ultrasonic reflection signals from the at least one material interface, provided at the bond area 3.

In the embodiment as shown in a simplified and schematic representation in FIG. 11, one ultrasonic transmitter and one ultrasonic receiver are integrated within a single ultrasonic transmitter/receiver head 12. The head 12 incorporates a first converter 14a which is an electrical to mechanical converter and which converts electrical input signals applied at input $E_{12}$ into ultrasonic signals, which are focused as a beam on the bond area 3. The converter 14a is operationally connected at its electrical input $E_{12}$ to an electrical oscillator 16. Oscillator 16 has a modulation control input Mod.

The head 12 further comprises a second converter 14b, which is a mechanical to electrical converter and which converts ultrasonic input signals into electrical output signals at its output, being operationally connected to the output $A_{12}$ of the head 12.

The two converters 14a and 14b may be realized by one single converter with a mechanical output/input and, accordingly, an electrical input/output, much in analogy to a microphone operable as a loudspeaker too. Within head 12 additional electronic units as e.g. for signal preamplification, analog to digital conversion, signal tailoring, filtering, electrical biasing and electrical supplying may be integrated (not shown).

The oscillator 16 is operated at an ultrasonic signal frequency, as e.g. at 10 MHz. Such ultrasonic frequency signal is amplitude-modulated to result in a pulse train of ultrasonic frequency impulses. The impulses are in fact envelopes of ultrasonic frequency signals, present during pulse duration. The pulse repetition frequency of these impulses of ultrasonic frequency signals may be selected in the KHz range. Preferably the duty cycle of the pulse train is selected to be short, e.g. 0.1 or smaller, which means that the pulse duration is short compared with the pulse repetition period.

Converted by the electrical to mechanical converter 14a there is thus generated a beam of a pulse train of ultrasonic signals S as schematically shown in FIG. 12. Therein As denotes the amplitude of the ultrasonic signal within the impulses I, $T_I$ the pulse repetition period and $\Delta$ the pulse duration. Duty cycle is defined by the ratio $\Delta/T_I$.

The beam of the pulse train of ultrasonic signals is focused onto the bond area 3. Thereby the bond area 3 is moved relative to the transmitter/receiver head 12, preferably at constant speed v as also shown in FIG. 3. Thus, the bond area 3 is sampled by the impinging ultrasonic pulse train beam in fact at a sampling rate which is given by pulse repetition frequency and speed v. Accordingly pulse repetition frequency and scanning speed v are selected in mutual dependency.

The impulse train of ultrasonic signals impinges first upon the material interface $Ph_0$ at the outer surface 10 normally exposed to ambient of the bonding area 3, then on any material interface below $Ph_1$, $Ph_2$ according to FIG. 11. If several material interfaces are present at the bond area 3, ultrasonic signal reflection occurs at all the interfaces.

Thus, at each of the interfaces Ph the impinging ultrasonic signal impulse train is reflected, The time delay $\tau$ or phasing $\Phi$ with which an impulse train reflected at a respective interface Ph impinges on the mechanical input of the mechanical to electrical converter 14b is dependent from which interface such impulse train comes from. A reflected impulse train from $Ph_0$ will impinge with a smaller time delay $\tau_1$ or phasing $\Phi_1$ on converter $14_b$ compared with the impulse train reflected from the next material interface $Ph_1$. Preferably the duty cycle of the transmitted ultrasonic impulse train S is selected so small that the impulse trains E reflected from the at least two interfaces $Ph_0$, $Ph_1$ impinge on converter $14_b$ well separated in time from and without overlapping the transmitted impulse train. This facilitates considerably echo or reflection exploitation. When the pulse repetition frequency and the duty cycle conditions are selected to result in overlapping echos and/or transmitter impulse train signals, separation of the respectively interesting echo pulse trains may be done by correlation techniques under consideration that for a given structure of bond area 3 and container 1 the time delays $\tau$ or phasings $\Phi$ from the material interfaces are known too.

In FIG. 13 there is schematically shown phasing $\Phi$ according to time delay $\tau$ of an echo ultrasonic pulse train E with respect to the transmitted pulse train S and the amplitude $A_E$ of such reflected pulse train. The reflected or echo pulse trains of at least two material interfaces $Ph_0$, $Ph_1$ impinge on converter $14_b$ with non-overlapping impulses with a predetermined, known phasing, e.g $\Phi_0$ for interface $Ph_0$, $\Phi_1$ from $Ph_1$ etc. Therefore, the output signal at $A_{12}$ from head 12 is operationally connected preferably to a number of time slot control units $16_0$, $16_1$, etc., the number of which according to the number of material interfaces Ph wherefrom the echo shall be evaluated. The time slot units 16 provide for signal communication from their input to their output during a predetermined measuring time $\Delta t$ initiated with a respective time lag $\tau_0$, $\tau_1$, ... from the raising edge of the impulses at the output of oscillator 16. Thus, after the time span $\tau_0$ slightly shorter than the expected time lag of the echo signal from interface $Ph_0$ unit $16_0$, in fact as a switching unit, provides signal communication between its input and its output during a measuring time span $\Delta t$ and it is after $\tau_0$ according to $\Phi_0$ and during measuring time slot $\Delta t$ that the echo impulse train $Ph_0$ will appear at the output of unit $16_0$. Accordingly the respective echo impulse trains are selected and separated. As schematically shown in FIG. 11 the respective interface-specific echo signals are fed to respective units $18_0$, $18_1$, ... which respectively generate at their outputs first signal $S(\Phi)$ dependent on the exact time lag or phasing $\Phi$ of the respective echo signals and $S(A)$ dependent on the amplitude e.g. the average amplitude or the peak amplitude of the respective echo signal impulses. The phase or time lag dependent signal $S(\Phi)$ is fed to a differentiating unit $20_{0\Phi}$, whereas the amplitude-dependent signal $S(A)$ is fed to a differentiating unit $20_{0A}$.

At the respective units 20 there is formed the time derivative of phase-dependent and/or amplitude-dependent signals of the echo signal from one material interface to be evaluated. The time derivative signals at the outputs of the units 20 are input to comparator units 22 where the respective momentarily prevailing time derivative is compared with a preset, preferably adjustable threshold value (not shown). Whenever the instantaneously prevailing time derivative crosses the threshold value there is generated at the outputs of the units 22 an indicative signal indicating that along the bond area 3 there has been found an inaccuracy.

Because in most cases it is of no interest whether such inaccuracy was detected due to amplitude and/or due to phasing, preferably the output signals of the units 22 are operationally connected to a central evaluation unit 24, which generates at its output a signal IB indicating "inaccurate bonding".

In FIG. 11 the principles of the sensing technique according to one aspect of the present invention have been explained in analog technique. Nevertheless, it is perfectly clear to the skilled artisan that by respective analogue to digital conversion of signals depending from the ultrasonic signals, the signal evaluation may be performed digitally. Thereby it might be useful to convert such digital signals from time domain into frequency domain and to perform signal evaluation in frequency domain by performing e.g. Fast Fourier Transform (FFT) upon the digital signals.

Whenever the above mentioned "inadequate bonding" signal IB is generated at unit 24, the respective container under test is removed from further use, so that the remaining containers may be said to have all adequate bond along their bond areas 3.

According to FIG. 11 the echo signals have been shown to be evaluated with respect to their time lag or phasing as well as with respect to their amplitudes. Nevertheless it might be possible for some applications of the present invention to perform signal evaluation only by evaluating either echo time lag (phasing) or amplitude behavior.

Further, according to FIG. 11 and the above explanations the echo signals from more than two material interfaces Ph may be exploited. Nevertheless, it has been found that the most important material interface is that—$Ph_0$—at surface 10, which is normally exposed to ambient. Therefore, it might be possible and simplifies the overall system significantly, just to exploit echo signals which arise at the material interface $Ph_0$.

Thereby with an eye on FIG. 11 only the time slot unit $16_0$ is necessary and the further evaluation units operationally linked thereto.

In a most preferred embodiment and as shown in FIG. 11 at 26, there is provided on one hand between the mechanical output of the electrical to mechanical transducer $14_a$ and between the mechanical input of the mechanical to electrical transducer $14_b$ and the surface 10 normally exposed to ambient of the bonding area 3 on the other hand a material medium which is different from air. In a most preferred embodiment such a medium 26 is a liquid medium, thereby most preferably water. Thereby, it is important to provide such liquid without gas bubbles to avoid creating additional material interfaces and thereby noise. Further, according to FIG. 11 transmission of the ultrasonic impulse train beam S and receiving the ultrasonic echo impulse train E is performed in a direction which is perpendicular to the medium plane $E_3$ of the bond area 3. This arrangement is preferably improved in that the direction of transmitting the beam of ultrasonic impulse train as well as direction, preferably coaxially thereto, of highest sensitivity of the mechanical to electrical converter 14b tilted by an angle α with respect to the normal n upon medium plan $E_3$. In FIG. 14 the band-shaped bond area 3 is exemplified with the normal n on the medium plane $E_3$ as at least locally defined by the bond area 3. Thereby α is defined in a plane $E_α$ which contains n and is parallel to the direction of scanning speed v. According to FIG. 11 transmittance of the ultrasonic beam as well as reception occurs in direction n according to FIG. 14. In a most preferred embodiment nevertheless the direction of the ultrasonic beam S as well as of highest sensitivity of reception, and thus according to E of FIG. 11, is tilted with respect to the normal n by an angle α, for which there is valid:

$$0<α≤30°,$$

thereby preferably $$5≤α≤20°$$

and especially preferred $$10≤α≤18°$$

In FIG. 15 there is schematically shown the bond area 3 and along such bond area 3 entrapped material and/or air 28. Such inadequate bond leads to surface 10 having a buckle. Practically all kinds and types of bond inaccuracies lead to such kind of geometric deformation of the outer surface 10 at the bond area 3. When in the preferred mode the axis of ultrasonic impulse train beam S and reception E, according to FIG. 14, is tilted by an angle α, the change of reflection at $Ph_0$ when the ultrasonic beam scans along the bond area 3 is amplified and thus its time derivative, Whereas at an angle α and considering a v direction as shown in FIG. 15, first a surface area 28a, which is bent towards the axis $A_B$ of S and E, will increase the sensed reflected amplitude, in the subsequent area 28b, such amplitude will be considerably reduced. Thereby, there will occur an amplified d/dt of the sensed signal, especially as concerns its amplitude, when the ultrasonic beam scans along the surface areas 28a, 28b.

Thus, by tilting the axis $A_B$ of ultrasonic beam transmittance and of reception there is reached an amplified response to geometric inaccuracies especially along $Ph_0$. From FIG. 15 it becomes apparent too that if reflections are also exploited from other material interfaces, e.g. $Ph_1$ of FIG. 15, also these echo signals will have an amplified time derivative response due to the tilting angle α.

It has to be noted that in a configuration as shown in FIG. 15 of bond inaccuracy additionally there will locally be generated additional material interfaces, which might be additionally detected.

In FIG. 16 there is shown, still simplified and schematically by means of a functional block/signal flow diagram in analogy to the representation of FIG. 11, a further improvement and preferred form of the system as was explained with the help of FIG. 11. Thereby, it is recognized that it would often be desirable not only to generically detect that the bonding along a bond area 3 is inaccurate but also to detect where such inaccurate bond is present along the bond area 3. To do so according to FIG. 16 scanning the bond area 3 by the ultrasonic impulse train beam is started at a predetermined position PosΦ of the bond area 3.

There is e.g. provided a time counter unit 30, e.g. clocked by the output of oscillator 16, which is disabled when a signal "inaccurate bonding"—IB—is generated at the output of unit 24 as of FIG. 11. Because the speed v of relative movement between transmitter/receiver head 12 and bond area 3 is predetermined and known, an evaluation unit 32 can calculate from the time up to occurrence of an "inadequate bond"—IB—signal and the preset speed v, the location $x_E$ along bond area 3, at which a bond failure or bond inaccuracy was detected.

Thereby, it becomes possible to install a feedback frog bond failure detection to a bonding station, especially if at a predetermined number of subsequent containers under bond accuracy test such bond inaccuracies occur at the same location of the bond area. This may be a valuable information about inaccuracy of the bonding station as e.g., of the bonding tools.

Liquid Interlayer

As has been discussed in context with the sensing technique applied according to the present invention that in a most preferred embodiment there is applied between the mechanical output of an electrical to mechanical converter for generating ultrasonic energy and between the mechanical input of a mechanical to electrical converter to sense ultrasonic energy on the one hand and the outermost surface 10 of a bond area 3 to be investigated, an intermediate medium, preferably of a liquid and thereby most preferably of water.

According to FIG. 17 in a first preferred embodiment to do so an ultrasonic transmitter/receiver head 34, preferably a head 12 as was explained with the help of FIG. 11, is placed in a water bath 36, wherein at least the bond area 3 of a container 1 to be tested is also immersed.

Thereby, as was also explained in context with the system according to FIG. 11, there is installed a relative movement v between the head 34 and the bond area 3 for ultrasonically scanning along the entire bond area 3. Preferred techniques of installing such relative movement also in a bed of liquid will be addressed later.

In FIG. 18 there is shown a second preferred embodiment to realize a liquid and especially preferred water ultrasonic conductor between the active transmitter/receiver surfaces of a head 38 and the bond area 3. A liquid, and especially preferred a water supply duct system 40 provides for liquid 42 downstream the active transducer and receiver surfaces of the transducer/receiver converters, The casing of the head 38 provides for an outlet nozzle 44 through which besides of the ultrasonic beam and the echo signals a liquid film 46 is dispatched over a limited area of the bond area 3. A suctioning head 48 is arranged adjacent to the bond area 3 and is connected to a pump (not shown). The liquid film dispatched upon the bond area 3 is removed by the suctioning head 48 shortly after head 38 has scanned the liquid-covered part of the bond area 3. In FIG. 18 the relative movement v of head 38 relative to and along bond area 3 is again shown.

Control of Relative Movement Between Ultrasonic Transmitter/Receiver and Bond Area In FIG. 19 a first preferred embodiment of realizing such relative movement is shown. Thereby, the container 1 and the bond area 3 are of rotational symmetric shape with respect to a central axis Z. The container 1 is positioned on a rotational drive 50, coaxially to its central axis Z, with a drive motor 52 and preferably a rotational angle detector 54. By means of the drive unit 50 the container 1 is rotated preferably at constant rotational speed ω. Preferably rotation is started when a predetermined marking M at the container 1 assumes a predetermined rotational position, φ=0. Relative to that position the rotational angle detector 54 generates a signal φ indicative of the angle instantaneously achieved.

Measurement of that angle allows location of an inaccurate bond along bond area 3 once detected by stationary ultrasonic transmitter/receiver 54 as was explained more generically in context with FIGS. 11 to 18.

In the sense of mechanical inversion FIG. 20 shows an analog arrangement, whereat instead of the container 1 the ultrasonic transmitter/receiver 54 is rotated about central axis Z of container 1 by means of a drive unit 58 with a drive motor 60 and a rotational angle detector 62.

Both embodiments may be realized in combination with either water bath technique as of FIG. 17 or water dispatching technique as of FIG. 18 as well as with the technique of tilting the axis of ultrasonic beam as was explained in context with FIGS. 14 and 15. Further preferably the transmitter/receiver 54 is conceived as was generically explained with the help of FIG. 11 with according signal evaluation.

These preferred combinations with previously addressed techniques are also valid for the further embodiments of relative movement control exemplified below.

A further preferred embodiment thereof is schematically shown in FIG. 21. Here the container 1 with any kind of shape of bond area 3 as schematized in FIG. 21 is stationary. The transmitter/receiver 54 is mounted to an x/y linear drive being as schematically shown movable in x direction driven by a motor $56_x$ and in y direction in dependency from a drive in x direction by means of a motor drive $56_y$. As whenever containers of the addressed kind are to be tested with respect to their bond area 3 the shape of the bond area 3 is known and the speed $v_{xy}$, with which the transmitter/receiver 54 shall scan the bond area 3, is predetermined, the drives $56_x$ and $56_y$ are controlled by a control unit 58 to perform at the preselected speed $v_{xy}$ a course which accords to the bond area 3 to be investigated. In unit 58 the scanning movement is preprogrammed. The predetermined speed $v_{xy}$ and the known course $p_{3xy}$ of the bond area are input to unit 58. By this technique it is possible to scan practically any shape of two-dimensional bond area which may be most complex.

In analogy to the transition from the embodiment of FIG. 19 to FIG. 20 i.e. by mechanical inversion, it is perfectly clear that also the embodiment of FIG. 21 may be mechanically inverted in that the transmitter/receiver 54 is kept stationary and, instead, the container 1 is moved along two coordinate directions x and y.

In FIG. 22 a further preferred embodiment is shown schematically. The container 1 with the bond area 3 to be investigated is deposited on a rotational drive arrangement most similarly to that of FIG. 19. Further, the ultrasonic transmitter/receiver 54 is mounted linearly movable, parallel to the plane wherein the course of the bond area 3 substantially resides. Rotation of the container 1 and linear movement of the transmitter/receiver 54 are controlled via respective drives $60_r$ and $60_\omega$ in mutual dependency. Again the desired speed $v_{xy}$ as well as the path or shape $p_{3xy}$ of the bond area as predetermined and known respectively are input to the control unit 62, the output of which controlling the drives $60_r$ and $60_\omega$.

Often the course of bond area 3 of containers is not identical for all containers of a type considered, but relatively large differences are encountered from one container to the other, e.g. due to manufacturing tolerances. In such a case it might be difficult to control scanning operation of the bond area 3 by means of the ultrasonic transmitter/receiver by preprogrammed or preset movement courses. In FIG. 23 there is again schematically shown an embodiment of such movement control whereat generically the course of the bond area 3 is traced and such tracing controls automatically the movement of the transmitter/receiver 54. According to FIG. 23 there is provided a tracing head 62 which may be realized e.g. as a picturing head as with CCD optoelectric conversion, may be a laser tracing head, an infrared tracing head etc. The head 62 recognizes the location of the bond area 3, which might have as shown in FIG. 24 and in a cross-sectional representation according to X—X of FIG. 6 the shape of a flat channel $3_a$. The head 62 is mounted or coupled to the transmitter/receiver 54, Again e.g. x/y drives $66_x$, $66_y$ are provided, which control x/y movement of transmitter/receiver 54 and tracing head 62. Via a control unit 64 which is at its input operationally connected to the tracing head 62, the x/y drives $66_x$ and $66_y$ are negative feedback controlled so that head 62 and transmitter/receiver head 54 follow bond area 3 at a desired, predetermined speed.

Looking back on the embodiment according to FIG. 21 the movement of transmitter/receiver 54 head is controlled electronically according to a predetermined known course of bond area 3. Instead on controlling such movement electronically it is further absolutely possible to provide a purely mechanical guiding path for transmitter/receiver head 54 as by a slot guiding rail and to drive the transmitter/receiver 54 at predetermined speed along such mechanical guiding rail.

Considering the embodiments of movement control as schematically shown by FIGS. 19 to 24 the skilled artisan will recognize other similar embodiments of such movement control depending on the kind of container and bond area shape to be investigated.

Although the present invention up to now has been described primarily on the assumption that the bond area is substantially planar, i.e. defines substantially a plane, it might occur the case where such bond area defines for a path which is three-dimensional. In such a case and without departing from the concept of the present invention and looking back on the exemplified embodiments of movement control a further dimension of relative bond area to ultrasonic transmitter/receiver movement is introduced, so that scanning of the bond area may be performed by three-dimensional movement.

Receptacle Positioning

In most embodiments to be realized for scanning the bond area 3 of a container 1 it is important to position the respective container 1 under investigation in a well-defined reproducible position. This is especially not obvious for containers where the shape may vary greatly due to manufacturing tolerances or to previous handling, as e.g. at plastic material containers. This is especially critical when realizing the relative movement of ultrasonic transmitter/receiver as exemplified in the FIGS. 19, 20, 21, 22, i.e. whenever such movement control is based on predetermined known and prestored path or shape of the bond area 3.

In FIG. 25 a preferred embodiment for properly positioning a container 1 to be investigated in a predetermined position is shown. There is provided for a container 1 of given shape a receiving frame 68 with a sidewall 70 and a bottom surface 72. For positioning a container 1, which has a planar rim or abutment 72 adjacent to or formed by the bond area 3, the height h of the sidewall 70 is constant all around bottom surface 72. Nevertheless, this needs not necessarily be the case as for containers, which have a positioning rim or abutment adjacent to or formed by the bond area 3 which is not planar.

There is provided an evacuation line 74 which abuts into the cavity formed by the walls 70 and the bottom surface 72, which line is connected to a suctioning pump (not shown). Thereby, a container 1 introduced into the cavity 71 is firmly drawn by suction into cavity 71 and firmly positioned in a predetermined position. The arrangement as of FIG. 25 is conceived symmetrical to a central axis Z because the container 1 shown and to be positioned with that arrangement is symmetrical to such axis Z. Nevertheless, it must be understood that the shape of the cavity 71 is adapted to the respective shape of a container 1 to be investigated and may thereby be of any shape according to that of the container.

The arrangement as of FIG. 25 or similar may be operated stationarily or rotating or linearly moving in a driven manner so as to realize the movement control embodiments as were exemplified above. Further, the arrangement as of FIG. 25 or similar may be applied for the technique where, according to FIG. 17, container and transmitter/receiver are immersed into a liquid bath, thereby preferably into a water bath, or may be applied in combination with the technique as shown in FIG. 18, where only locally a liquid cushion, thereby preferably a water cushion, is established between the active transmitter and receiver surfaces of the ultrasonic transmitter/receiver head and the bond area 3 to be investigated. If necessary and as shown in FIG. 26 there might be provided at the wall 70 of the arrangement of FIG. 25 a support 76, which directly supports a rim 78, whereat the bond area 3 is formed. This support 76 may be provided either by distinct, either locally support parts distributed along the periphery of the front end of wall 70 or forming a continuous ring along that front end. Such supports may be of an elastomer material.

It further might be advisable to provide sealing members as of elastomeric seals 80 along the inner surface of the wall 70 to make sure that the outer surface of the container's wall form together with the internal surface of wall 70 a substantially tight compartment 71.

Inline Manufacturing of Containers with Approved Bond

In FIG. 27 there is shown in form of a schematic representation an overall plant for manufacturing filled containers with tested and approved bond. As schematically shown and with an eye e.g. on FIG. 1, first parts 1a of the containers are conveyed as a stream by means of a linear or a rotary conveyor as by means of a carousel conveyor generically shown at 82 towards and into a filling and assembling station 84. To the assembling and filling station 84 a product $P_r$ is fed as well as, by means of a suited conveyor 84 as outlined above, and again with an eye on FIG. 1, second parts 1b of the containers.

In station 84 product $P_r$ is filled into at least one of the two parts 1a and/or 1b and the two parts are assembled by generating a bond along a bond area 3. By means of a further suited conveyor 88, which again may be a linear conveyor or a rotary conveyor as e.g. and preferably a carousel conveyor, the assembled and filled containers 1 with the two parts 1b, 1a linked via bond area 3 are conveyed towards and into a bond testing unit 90. Therein the bond area 3 of all the containers conveyed to station 90 by means of conveyor 88 are scanned on bond inaccuracies as was explained with the help of the FIGS. 1 to 26. Containers at which an inaccurate, improper bonding along the one or more than one bonding areas is detected in unit 90 by ultrasonic examination are removed as shown at 92. As was explained preferably an information 1 is output from unit 90 indicative of where the respectively found bond inaccuracies were present along the respective bonding areas 3. Possibly this information is automatically fed back to the bonding operation in unit 84 for remedying automatically such inaccuracies.

Thus, by the plant according to FIG. 27 filled containers, assembled by bonding along a bonding area are manufactured, which show up tested bonding areas found as being accurately manufactured.

According to FIG. 28 the plant as of FIG. 27 is thereby preferably improved for overall testing in that by means of conveyor 94, which again may be a linear or a rotary conveyor as e.g. and preferably a carousel conveyor, the containers 1 which have been found perfect with respect to bond along their bonding areas 3 are conveyed to a leak test station 96, whereat leakage of the overall containers 1 is tested. Containers which are found to be leaky are again removed as shown at 98, and containers 1 which are unleaky and which as well have an accurate bond along their bonding areas are conveyed by a further linear or rotary conveyor as by a carousel conveyor 100 for further use. Thereby possibly the sequence of bond testing and then leak testing may be inverted to first leak testing and then bond testing. Leak testing of the filled and closed containers may thereby be performed as e.g. described in one or more than one of the following patents of the same applicant: U.S. Pat. No. 5,029,464, U.S. Pat. No. 5,170,660, U.S. Pat. No. 5,239,859, U.S. Pat. No. 5,915,270 and especially U.S. Pat. No. 6,082,184, U.S. Pat. No. 6,202,477, U.S. Pat. No. 5,907,093, which are all integrated in the present description by reference with respect to leak testing of the containers 1.

Thus, with a plant consisting of the embodiment of FIGS. 27 and 28 overall testing of the containers 1 on appropriate bonding and on appropriate tightness is performed.

What is claimed is:

1. A method of manufacturing filled containers comprising the steps of:
    providing at least a first and a second part of the container;
    providing a product within at least one of said first and said second parts;
    assembling said first and said second parts by bonding a portion of said first part to a portion of said second part, thereby generating a bond area;
    scanning along said bond area with a transmitted beam of a pulse train of ultrasonic energy;
    sensing a reflected pulse train of ultrasonic energy from said bond area;
    determining time derivative of at least one of time lag and of amplitude of said sensed pulse train;
    generating a signal indicative of the quality of said bond along said bond area by comparing at least one of said time derivatives with a predetermined threshold value;
    separating said container if said indicative signal indicates a bond along said bond area being inaccurate.

2. The method of claim 1, further comprising the step of leading said beam of a pulse train towards and onto said bond area and leading said reflected pulse train from said bond area at least to a predominant part exclusively through a liquid.

3. The method of claim 1, further comprising the step of directing said beam of a pulse train in a direction towards and onto said bond area, which is different from perpendicularly thereto considered in a plane defined by a perpendicular line on said area and scanning direction of said beam along said bond area.

4. The method of claim 1, wherein said bond area at said container forms a loop.

5. The method of claim 4, wherein said loop is at least substantially planar.

6. The method of claim 4, wherein said loop is at least substantially circular.

7. The method of claim 1, wherein said bond area defines for at least three materials stacked one upon the other, whereby respectively two of said materials concomitantly form a material interface, said sensing comprising sensing a reflected pulse train of ultrasonic energy from at least one of said material interfaces.

8. The method of claim 1, further comprising monitoring the scanned path of said pulse train of ultrasonic energy along said bond area and identifying the location along said bond area at which said indicative signal generated indicates an inaccurate bond.

9. The method of claim 1, wherein said beam is generated substantially coaxially to an axis of highest sensitivity of ultrasonic energy sensing.

10. The method of claim 1, further comprising selecting duty cycle and pulse repetition frequency of said pulse train so that said pulse train transmitted does not overlap said at least one reflected pulse train as sensed.

11. The method of claim 3, further comprising selecting said direction to define with said perpendicular direction an angle α for which there is valid:

$$0°<\alpha\leq 30°,$$

preferably $$5°\leq\alpha\leq 20°,$$

and even more preferred $$10°\leq\alpha\leq 18°$$

12. The method of claim 2, said liquid being water.

13. The method of claim 2, further comprising the step of immersing at least said bond area of said container and the output of an electrical to mechanical converter for generating said beam of a pulse train as well as the input of a mechanical to electrical converter for sensing said reflected pulse train into said liquid.

14. The method of claim 2, further comprising establishing a local bridge of said liquid from an output of an electrical to mechanical converter for generating said beam of a pulse train to said bond area and to an input of a mechanical to electrical converter for sensing said pulse train.

15. The method of claim 14, further comprising the step of establishing said bridge by applying said liquid locally on said bond area and suctioning said liquid from said bond area after having been subjected to said scanning.

16. The method of claim 1, further comprising establishing said scanning by moving said beam along said bonding area, thereby keeping said container stationary.

17. The method of claim 1, further comprising the step of scanning said bond area by moving said beam along said bond area keeping said beam stationary.

18. The method of claim 1, further comprising the step of performing said scanning by moving said container as well as said beam.

19. The method of claim 1, further comprising the step of performing said scanning along a predetermined trajectory.

20. The method of claim 1, further comprising the seep of performing said scanning by tracing the course of said bond area and controlling the relative movement of said container and of said beam by a result of said tracing.

21. The method of claim 1, further comprising the step of positioning said container for said scanning by suctioning.

22. The method of claim 1, further comprising the step of feeding a stream of said first and second parts to said providing said product within at least one of said parts, said assembling, said scanning, sensing, determining and generating, thereby separating containers for which the respective indicative signal indicates an inadequate bond from the other containers and conveying the other containers to leak testing, thereby separating from said other containers containers being found leaky.

23. A method of manufacturing filled containers comprising the steps of providing at least a first and a second part of the container;

providing a product within at least one of said first and said second parts;

assembling said first and said second part by bonding a portion of said first part to a portion of said second part, thereby generating a bond area;

scanning said bond area with a transmitted beam of ultrasonic energy;

sensing reflected ultrasonic energy from said bond area;

generating from said sensed ultrasonic energy a signal indicative of quality of said bond along said bond area, thereby leading said ultrasonic energy from a mechanical output of an electric to mechanical converter to generate said transmitted beam and onto said bond area and said reflected ultrasonic energy from said bond area towards and onto a mechanical input of a mechanical to electrical converter for sensing said reflected ultrasonic energy in a liquid.

24. The method of claim 23, further comprising performing time differentiation of at least one characteristic value of said reflected ultrasonic energy and generating from the result of said time differentiation said indicative signal.

25. The method of claim 23, further comprising the step of directing said scanning ultrasonic energy as a beam of a pulse train towards and onto said bond area.

26. The method of claim 23, thereby directing said beam of ultrasonic energy in a direction towards and onto said bond area, which is different from perpendicularly considered in a plane defined by a perpendicular line on said area and scanning direction of said beam along said bond area.

27. The method of claim 23, wherein said bond area forms a loop.

28. The method of claim 27, wherein said loop is at least substantially planar.

29. The method of claim 27, wherein said loop is at least substantially circular.

30. The method of claim 23, wherein said bond area defines for at least three materials stacked one upon the other, whereby respectively two of said materials concomitantly form a material interface, said sensing comprising sensing reflected ultrasonic energy from at least one of said material interfaces.

31. The method of claim 23, further comprising monitoring the scanned path of said transmitted beam along said bond area and identifying a location along said bond area at which said indicative signal generated indicates an inaccurate bond.

32. The method of claim 23, wherein said beam is generated substantially coaxially to an axis of highest sensitivity of ultrasonic energy sensing.

33. The method of claim 25, further comprising the step of selecting duty cycle and pulse repetition frequency of said pulse train so that a pulse train transmitted does not overlap a reflected pulse train of ultrasonic energy.

34. The method of claim 26, further comprising selecting said direction to define with said perpendicular direction an angle α for which there is valid:

$0° < \alpha \leq 30°$, preferably $5° \leq \alpha \leq 20°$, and even more preferred $10° \leq \alpha \leq 18°$.

35. The method of claim 23, wherein said liquid is water.

36. The method of claim 23, further comprising the step of immersing at least said bond area of said container and an output of an electrical to mechanical converter for generating said beam as well as the input of a mechanical to electrical converter for sensing said reflected energy into said liquid.

37. The method of claim 23, further comprising establishing a local bridge of said liquid from an output of an electrical to mechanical converter for generating said beam to said bond area and to an input of a mechanical to electrical converter for sensing said reflected ultrasonic energy.

38. The method of claim 37, further comprising the step of establishing said bridge by applying said liquid locally on said bond area and suctioning said liquid from said bond area after having been subjected to said scanning.

39. The method of claim 23, further comprising establishing said scanning by moving said beam along said bonding area, thereby keeping said container stationary.

40. The method of claim 23, further comprising the step of scanning said bond area by moving said beam along said bond area, keeping said beam stationary.

41. The method of claim 23, further comprising the step of performing said scanning by moving said container as well as said beam.

42. The method of claim 23, further comprising the step of performing said scanning along a predetermined trajectory.

43. The method of claim 23, further comprising the step of performing said scanning by tracing the course of said bond area and controlling the relative movement of said container and of said beam by a result of said tracing.

44. The method of claim 23, further comprising the step of positioning said container for said scanning by suctioning.

45. The method of claim 23, further comprising the step of feeding a stream of said containers to said providing of said first and said second part, said providing said product within at least one of said parts, said assembling, said scanning, sensing, generating, leading, thereby separating container for which the respective indicative signal indicates an inadequate bond from the other containers and conveying the other containers to a leak testing, thereby separating from said other containers containers being found leaky.

46. A method of manufacturing filled containers comprising the steps of
providing at least a first and a second part of the container;
providing a product within at least one of said first and said second part;
assembling said first and said second part by bonding a portion of said first part to a portion of said second part, thereby generating a bond area;
scanning said bond area with a transmitted beam of ultrasonic energy;
sensing reflected ultrasonic energy from said bond area;
generating from said sensed ultrasonic energy a signal indicative of quality of said bond along said bond area, thereby
directing said beam of ultrasonic energy in a direction towards and onto said bond area which is different from perpendicularly thereto considered in a plane defined by a perpendicular line on said area and scanning direction of said beam along said bond area.

47. The method of claim 46, further comprising performing time differentiation of at least one characteristic value of said reflected ultrasonic energy and generating from the result of said time differentiation said indicative signal.

48. The method of claim 46, further comprising the step of directing said scanning ultrasonic energy as a beam of a pulse train towards and onto said bond area.

49. The method of claim 46, wherein said bond area forms a loop.

50. The method of claim 49, wherein said loop is at least substantially planar.

51. The method of claim 49, wherein said loop is at least substantially circular.

52. The method of claim 46, wherein said bond area defines for at least three materials stacked one upon the other, whereby respectively two of said materials concomitantly form a material interface, said sensing comprising sensing reflected ultrasonic energy from at least one of said material interfaces.

53. The method of claim 46, further comprising monitoring the scanned path of said transmitted beam along said bond area and identifying a location along said bond area at which said indicative signal generated indicates an inaccurate bond.

54. The method of claim 46, wherein said beam is generated substantially coaxially to an axis of highest sensitivity of ultrasonic energy sensing.

55. The method of claim 48, further comprising selecting duty cycle and pulse repetition frequency of said pulse train so that said pulse train transmitted does not overlap at least one pulse train reflected and as sensed.

56. The method of claim 46, wherein said direction is selected to define with said perpendicular direction an angle $\alpha$ for which there is valid:

$0° < \alpha \leq 30°$, preferably $5 \leq \alpha \leq 20°$, and even more preferred $10° \leq \alpha \leq 18°$.

57. The method of claim 46, further comprising leading said ultrasonic energy from a mechanical output of an electric to mechanical converter to generate said transmitted beam onto said bond area and said reflected ultrasonic energy from said bond area towards and onto a mechanical input of a mechanical to electrical converter for sensing said reflected ultrasonic energy in a liquid.

58. The method of claim 57, said liquid being water.

59. The method of claim 57, further comprising the step of immersing at least said bond area of said container and the output of said electrical to mechanical converter for generating said beam as well as the input of said mechanical to electrical converter for sensing said reflected energy into said liquid.

60. The method of claim 57, further comprising establishing a local bridge of said liquid from said output of said electric to mechanical converter for generating said beam to said bond area and to said input of said mechanical to electrical converter for said sensing.

61. The method of claim 60, further comprising the step of establishing said bridge by applying said liquid locally on said bond area and suctioning said liquid from said bond area after having been subjected to said scanning.

62. The method of claim 46, further comprising establishing said scanning by moving said beam along said bonding area, thereby keeping said container stationary.

63. The method of claim 46, further comprising the step of scanning said bond area by moving said beam along said bond area, keeping said beam stationary.

64. The method of claim 46, further comprising the step of performing said scanning by moving said container as well as said beam.

65. The method of claim 46, further comprising the step of performing said scanning along a predetermined trajectory.

66. The method of claim 46, further comprising the step of performing said scanning by tracing the course of said bond area and controlling the relative movement of said container and of said beam by a result of said tracing.

67. The method of claim 46, further comprising the step of positioning said container for said scanning by suctioning.

68. The method of claim 46, further comprising the step of feeding a stream of said first and second parts to said providing said product within at least one of said parts, said assembling, said scanning, sensing, generating and leading, thereby separating containers for which the respective indicative signal indicates an inadequate bond from the other containers and conveying the other containers to leak testing, thereby separating from said other containers containers being found leaky.

* * * * *